United States Patent
Feldman et al.

(10) Patent No.: US 6,809,808 B2
(45) Date of Patent: Oct. 26, 2004

(54) WAFER DEFECT DETECTION SYSTEM WITH TRAVELING LENS MULTI-BEAM SCANNER

(75) Inventors: Haim Feldman, Nof-Ayalon (IL); Emanuel Elyasaf, Rehovot (IL); Nissim Elmaliach, St. Raanana (IL); Ron Naftali, Shoham (IL); Boris Golberg, Ashdod (IL); Silviu Reinhorn, Mevaseret-Zion (IL)

(73) Assignee: Applied Materials, Inc., Santa Clara, CA (US)

( * ) Notice: Subject to any disclaimer, the term of this patent is extended or adjusted under 35 U.S.C. 154(b) by 0 days.

(21) Appl. No.: 10/103,560

(22) Filed: Mar. 22, 2002

(65) Prior Publication Data
US 2003/0179369 A1 Sep. 25, 2003

(51) Int. Cl.[7] .............................................. G01N 21/00
(52) U.S. Cl. .................................................... 356/237.1
(58) Field of Search .......................... 356/237.1–237.5, 356/600–601; 250/586, 559.42; 382/141, 253, 295, 296

(56) References Cited

U.S. PATENT DOCUMENTS

| | | | | |
|---|---|---|---|---|
| 5,633,747 A | * | 5/1997 | Nikoonahad | 359/312 |
| 6,236,454 B1 | * | 5/2001 | Almogy | 356/237.3 |
| 6,556,290 B2 | * | 4/2003 | Maeda et al. | 356/237.2 |
| 6,560,005 B2 | * | 5/2003 | Thomas | 359/305 |
| 6,578,961 B2 | * | 6/2003 | Vaez-Iravani | 356/237.2 |
| 2001/0048521 A1 | * | 12/2001 | Vaez-Iravani | 356/237.2 |
| 2002/0041374 A1 | * | 4/2002 | Ohshima et al. | 356/237.2 |
| 2002/0091323 A1 | * | 7/2002 | Dreher | 600/476 |
| 2003/0030886 A1 | * | 2/2003 | Thomas | 359/305 |

* cited by examiner

Primary Examiner—Michael P. Stafira
(74) Attorney, Agent, or Firm—Sughrue Mion PLLC

(57) ABSTRACT

A system for inspecting a specimen, such as a semiconductor wafer that uses a laser light source for providing a beam of light. The beam is applied to a traveling lens acousto-optic device having an active region and responsive to an RF input signal to selectively generate plural traveling lenses in the active region. The traveling lens acousto-optic device is operative to receive the light beam and generate plural flying spot beams, at the respective focus of each of the generated traveling lenses. A light detector unit, having a plurality of detector sections, each detector section having a plurality of light detectors and at least one multi-stage storage device operative to receive in parallel an input from the plurality of light detectors, is used to generate useable scan data. Information stored in each of the storage devices is serially read out concurrently from the multiple stages.

25 Claims, 7 Drawing Sheets

System Schematic Diagram

System Schematic Diagram

WAFER DEFECT DETECTION SYSTEM WITH TRAVELING LENS MULTI-BEAM SCANNER

TECHNICAL FIELD

The present invention relates to wafer defect detection systems which use a scanning laser beam to illuminate a wafer under analysis and identify defects by analysis of reflected light or transmitted light. In particular, the present invention concerns a scanner system using multiple beams that concurrently illuminate a sample such as a wafer, a reticle, a mask and the like, under inspection and generate multiple corresponding reflected or transmitted beams that are concurrently detected.

BACKGROUND ART

A variety of systems are used for automated inspection of semiconductor wafers, in order to detect defects, particles and/or patterns on the wafer surface as part of a quality assurance process in semiconductor manufacturing processes. It is a goal of current inspection systems to have high resolution and high contrast imaging in order to provide the reliability and accuracy demanded in sub-micron semiconductor manufacturing processes. However, it is also important to have a high-speed process that permits a large volume throughput so that the quality and assurance processes do not become a bottleneck in the wafer production process. Accordingly, the optical inspection systems must use shorter wave lengths, higher numerical aperture optics and high density image capture technology in order to enable the processing of data from such systems at sufficiently high rates that will satisfy the desired product throughput requirements.

A conventional imaging architecture that is used in wafer inspection systems at this time utilizes a single spot scanning laser for high-speed imaging. However, the data rates achievable by such architectures are limited by the physical constraints that arise due to limitations in the speed and quality of the single laser beam, the applicable optical system and related detection devices. For example, the single laser acting as a point light source is focused as a spot onto the object under inspection and is scanned across the surface of the object, which may be stationary or moved on a stage mechanism in coordination with the scan. The reflected light from the object is then imaged onto a detector, which generates pixel data from the scanning process. The detector may be a CCD array, whose individual elements are positioned to receive the reflected light as the beam is scanned and be read our serially, in a conventional fashion. While a high resolution may be obtained from such point source illumination, the requirement to scan each point in the field in order to construct a viewable image subjects the system to a limitation on its throughput.

The scanning of the single laser beam may be accomplished by a rotating mirror system, as seen in U.S. Pat. No. 5,065,008 or an acousto-optic cell. However, these single spot scanning architecture necessarily have a limited speed and are possibly subject to scan aberrations, low illumination brightness and potential thermal damage to the specimen when high brightness laser sources are used. The high data rates required to inspect the submicron structures of current semiconductor products cannot be achieved, even when a stage-type scanning system is used that moves the specimen relative to a fixed illumination and image location while a synchronized scanning pattern is produced by moving the single point of light over an area at the fixed location.

Accordingly, there is a need for a specimen scanning system that will improve specimen throughput, while maintaining or even improving the reliability and accuracy of the data collected during the scan of a specimen, whether in a stationary or stage-type system. This need is satisfied by the present invention, by utilizing a plurality of parallel scanning beams to scan a specimen and by detecting a plurality of parallel reflected beams or parallel transmitted beams, depending on whether the specimen is to be inspected by reflecting light from a surface or by passing light through a surface, and processing the plural reflected or transmitted beams concurrently, such that the throughput is significantly enhanced over the single spot scanned system.

SUMMARY OF THE INVENTION

The present invention involves a system for inspecting a specimen using a single light source that provides a beam of light. The beam of light is imaged onto a traveling lens acousto-optic device that has an active region and is responsive to an RF input signal to selectively generate plural traveling lenses in the active region. The traveling lens acousto-optic device is operative to receive the light beam and generate plural spot beams, at the respective focus of each of the generated traveling lenses. The system also includes a light detector unit, comprising a plurality of detector sections, each detector section having a plurality of light detectors and at least one multi-stage storage device operative to receive in parallel an input from the plurality of light detectors. The information stored in each of the multi-stage storage devices is serially read out concurrently from the multiple stages.

In accordance with another feature of the present invention, the invention involves a system for inspecting a specimen comprising a source of a plurality of scanning spot beams. The beams are imaged on a surface of the specimen and a plurality of beams are produced therefrom by reflection from or transmission through the specimen. A light detector unit, having a plurality of detector sections, each detector section having a plurality of light detectors and at least one multi-stage storage device operative to receive in parallel an input from the plurality of light detectors, is used. The information stored in each of the multi-stage storage devices is to serially read out concurrently from the multiple stages.

In accordance with yet another feature of the present invention, the invention involves a method for inspecting a specimen. The method includes providing a plurality of flying spot beams from a single source of light and scanning the plurality of spot beams on a surface of a specimen, whereby a corresponding plurality of beams are generated by reflection from or transmission through the specimen. Then, the content of each of the reflected beams is captured and stored simultaneously in a respective signal storage section. The stored information is serially read, thereby improving speed and throughput of scanned data.

A further feature of the present invention is the achievement of an acousto-optic device that is adapted to receive a source of light and an RF input for generating a plurality of traveling lenses that provide a plurality of concurrent scanned spots. The device comprises a crystal medium having an active region, the active region defining a direction of acoustic wave propagation, an RF input portion for receiving a RF chirped input and being disposed at one end of the medium in a direction of acoustic wave propagation and a light input portion for receiving light from the source of light, the light input portion being disposed transverse to the direction of acoustic wave propagation, and a light output portion. A series of RF pulses input to the RF input portion is operative to generate a sequence of traveling lenses concurrently existing in the active region, the traveling lenses being operative to receive the light input to the light input portion and generate plural spot beams output from the light output portion.

Another feature of the present invention is a method of operating an acousto-optic device having an active region and adapted to receive a source of light at a light input portion and an RF input portion for generating a plurality of traveling lenses that provide a plurality of concurrent spots from a light output portion. The method comprises inputting to the RF input portion a series of chirped input pulses whereby an acoustic wave is formed for each input pulse and propagates in the active region in a propagation direction, inputting to the light input portion light from the source and in a direction transverse to said propagation direction, and applying the light to the propagating acoustic waves, the waves forming traveling lenses and concurrently existing in the active region, each of the traveling lens being operative to focus and direct said light, whereby a respective spot beam for each lens is output from the light output portion.

Yet another feature of the present invention is a linear light detector unit for detecting a plurality of concurrently scanning spot beams. The light detector unit comprises a plurality of adjacent light detector sections disposed linearly along a common axis. Each of the detector sections has a plurality of adjacent light detectors, and at least one multi-stage storage device operative to receive in parallel an input from the plurality of light detectors and to serially read out information stored in the multiple stages.

A further feature of the present invention is a method for detecting a plurality of pixels stored in a linear CCD having a first plurality of sections, each section comprising a second plurality of pixel storage elements and receiving an input from a respective one of a third plurality of concurrently scanning beams. The method comprises capturing and storing the content of each of the third plurality of beams simultaneously in a respective signal storage section and concurrently serially reading out the stored signals.

A yet further feature of the present invention is an apparatus for detecting both bright field and dark field images from the surface of a specimen, where the bright field image is detected by at least one CCD and the dark field image is detected by at least one high sensitivity detector, such as a photomultiplier tube (PMT).

DETAILED DESCRIPTION OF THE INVENTION

The following detailed description is of exemplary embodiments of the invention but the invention is not limited thereto, as modifications and supplemental structures may be added, as would be apparent to those skilled in the art. In particular, but without limitation, while an exemplary embodiment may be disclosed with regard to the inspection of a specimen surface by detecting reflected light using a light source and detecting unit that are disposed on a common side of a specimen (a "reflective system"), it would be readily apparent to one skilled in the art that the teachings are readily adaptable to the inspection of a specimen by detecting transmitted light with a detecting unit that is on a side of a specimen opposite to that of the light source (a "transmissive system"). While the reflective system and the transmissive system differ, for one example by the absence of a beam splitter in the transmissive system, the principles of the present invention are applicable to both types of systems. As would be understood by one skilled in the art, both types of systems may be utilized separately or together in the inspection of a specimen, in accordance with the present invention.

Figure 1:
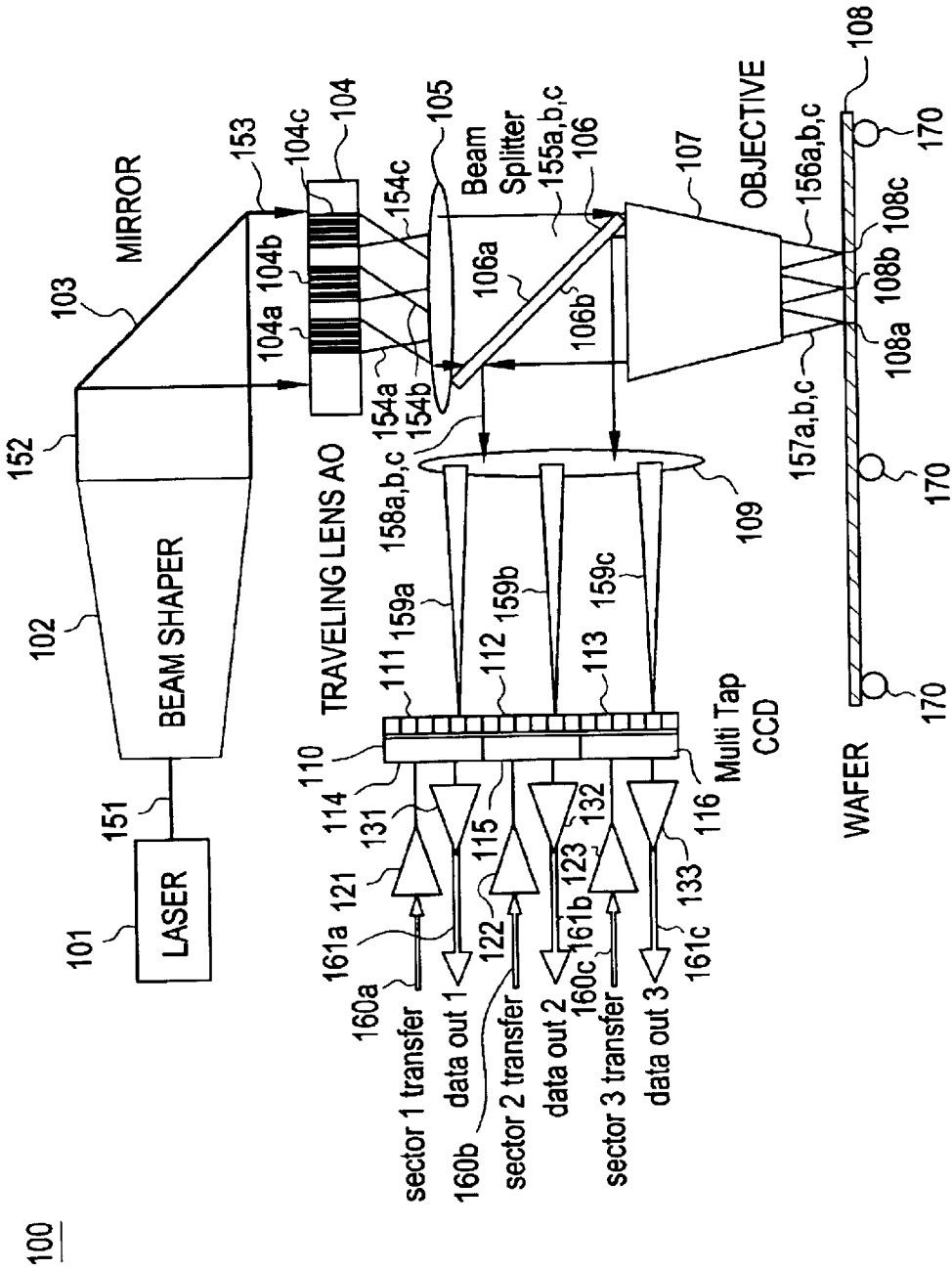
FIG. 1 illustrates a schematic representation of a first exemplary system and apparatus for scanning a wafer or other specimen in accordance with the present invention.

FIG. 1 is a schematic illustration of a wafer, reticule or similar specimen detection system 100 and apparatus utilizing a traveling lens multi-beam scanner in accordance with the present invention. Without limitation and only by example, the specimen may be any semiconductor product, such as 8 inch or 12 inch wafers or the like having multiple semiconductor devices thereon, at any of several stages of manufacture, or may be a mask, reticule or the like used in a manufacturing process, where such specimen must be inspected for defects, foreign objects or pattern accuracy. It is desirable in such systems to identify with high accuracy and reliability the size, location and type of structure, defect or object that appears on the specimen surface. It also is desirable to undertake such identification at high speed, in order to minimize the delay in the manufacturing process that is provided to the inspection and quality assurance steps.

The system 100 relies upon a bright light source, such as a CW (or pulse) laser 101 that produces a light beam output 151. The beam 151 is applied to a beam shaper 102 having a conventional design, which expands and collimates the beam 151 to form a beam 152 having a uniform intensity beam profile in a manner known in the art. For wafer inspection, the laser preferably operates at a short wavelength, for example, 248 nm or 193 nm, in order to produce high resolution, with stable output power (or stable pulse energy and pulse rate), a stable transverse mode and a stable beam pointing. The collimated beam 152 is applied to a conventional mirror 103, in order to shape and direct a beam 153 to an operational lens system, whose components will be described in greater detail subsequently.

In particular, the shaped beam 153 is projected onto a traveling lens acousto-optic device 104 that is operative to convert the shaped beam 153 into a plurality of beams 154a, 154b, 154c. While three beams are shown for convenience by way of example, the number of beams may be greater and in an exemplary embodiment may be ten or more concurrently scanning beams. The traveling lens acousto-optic device 104 is responsive to each of a series of chirped RF pulses, a single pulse resulting in the generation of a single lens and the series of pulses resulting in the formation of multiple cascaded lenses in the traveling lens device 104. Each lens will receive and focus the input laser light at its output, thereby forming the desired number of beams. As the RF pulses migrate through the device 104, the associated lenses will travel, causing each of their beams to move in the nature of a scan.

The basic theory, structure and materials of the acousto optic cell is taught in "Optical Scanning", edited by Gerald F. Marshall, Chapter 11 (published by Marcel Dekker, Inc. in 1991). As explained at pages 675–677, frequency chirp scanning of a single beam involves an acousto optic Bragg cell to which a linear frequency sweep (the "chirp") is applied. A frequency gradient produced across the optical aperture of the cell will act as a cylindrical lens whose focal length is based on the chirp rate. The light diffracted by the linearly swept acoustic frequency may be converging or diverging, and may be compensated by complementary optical lenses. In accordance with that disclosure, acousto optic scanners provide significant advantages in cost and performance, particularly where random access times are short. The acousto optic scanner typically generates one scanning beam, and where multiple beams are desired, as disclosed at pages 682–83 of Marshall's book, multiple chirp cells are required, each receiving chirped RF pulses. Specifically, when a linear increasing frequency is applied to the driver of each of a plurality of chirp cells in an array, a phase grating with pitch increasing in the time domain is set up as a continuous angle scan of each collimated beam of the array is produced according to the Bragg condition, thereby yielding a linear scan of the array of spots. At high frequency cutoff, the driver signal is set to zero, thereby allowing for dissipation of the acoustic energy in the chirp cells and resetting the spots before initiation of the next scan.

Two types of acoustic array scanners are taught in Marshall at pages 682–683, including one where bandwidth is multiplied and another where resolution is multiplied. In the first case, a large number of individually-driven, small and closely arranged transducers are mounted in parallel on an acousto optic medium made from $TeO_2$ glasses and from $PbMoO_4$ and $TeO_4$ crystals. The second case of acousto optic array involves an arrangement of the elements in series. The array of scanners, each with a particular resolution (points per line) can yield a greater resolution (points per line) by using complex optics.

By contrast, the acousto optic device 104 that is used in the present invention employs a single crystal that is effective to generate multiple traveling lenses based upon a series of input RF pulses. The single crystal in the device is composed of a material that is compatible with a UV light source, preferably having an acousto-optic medium made of fused silica, GaAs or $TeO_2$ glass, although other known materials having UV light compatibility, may be used. The crystal has an anti-reflective coating on each major side that rated at less than 0.5% for both sides. The device will operate in a longitudinal acoustic mode at a wavelength of 266 nm and at a center frequency of 200 MHz with a bandwidth of 130 MHz. RF power is less than 3.0 watts. The active aperture of the device may be 1.0 mm "H" by 60 mm "L" in one exemplary embodiment.

Figure 4:
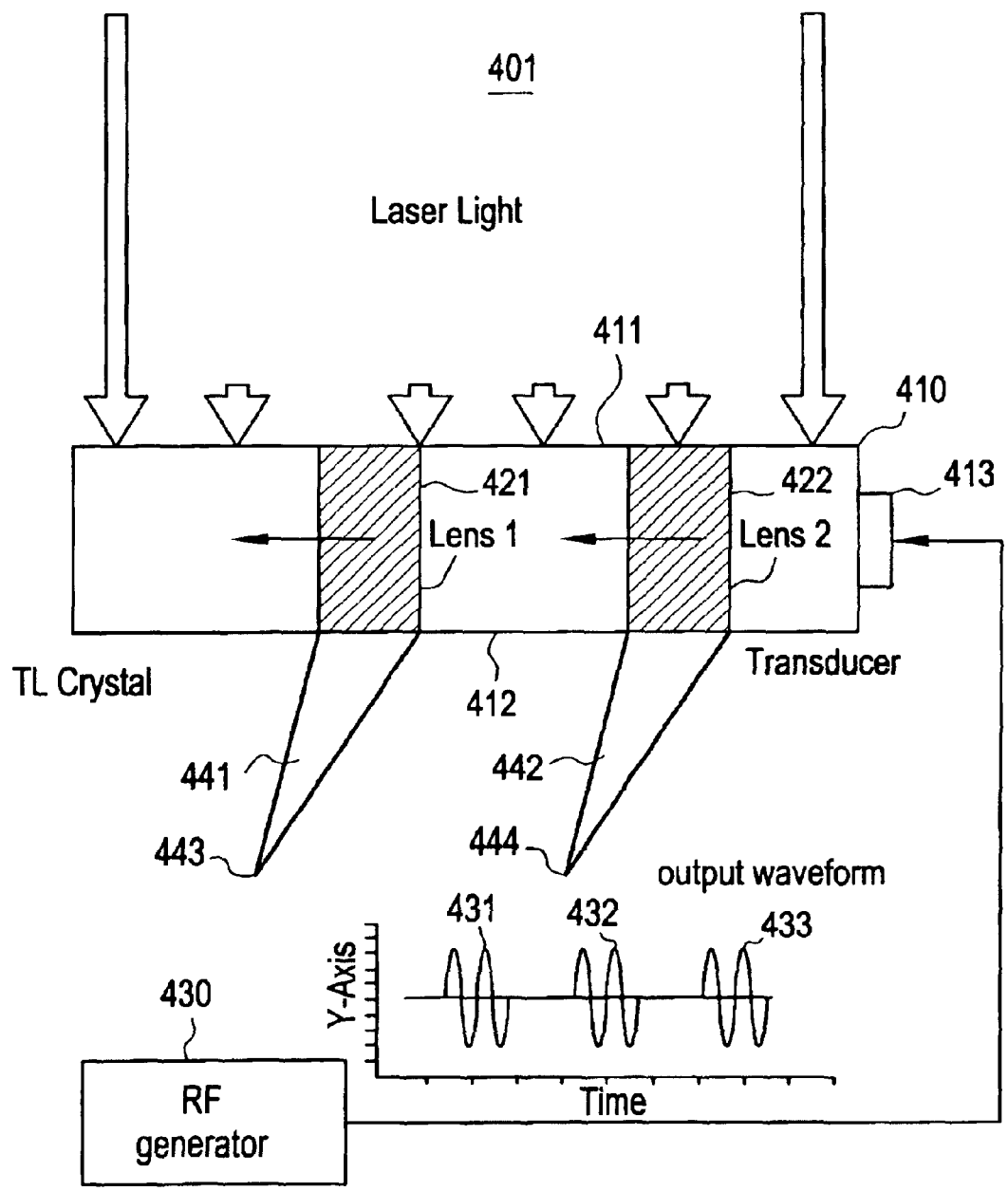
FIG. 4 is a schematic illustration of a traveling lens, multi-beam acousto-optic device, as used in an embodiment of the present invention.

In operation, as illustrated in greater detail in FIG. 4, laser light 401, which may be a single beam or a plurality of collimated beams as would be understood by one skilled in the art, would be applied to one major surface 411 of the transducer 410. An RF generator 430 provides a series of "chirps" or pulsed RF wave forms 431, 432, 433, etc., which optimally are identical in duration and amplitude an exemplary embodiment, but may differ in accordance with the desired optical effect of the traveling lens, to an RF input port (SNA connector) 413. The port is positioned to be transverse to the path of light and enables the RF waveforms to be injected at the edge of the crystal and to establish a pressure wave that traverses the length of the crystal at a velocity that, in an exemplary embodiment, is 5.96 mm/$\mu$s or approximately the speed of sound. The pressure waves that propagate through the crystal medium are aligned to provide cascaded focusing lenses 421, 422 for laser light 401 that passes into the input major surface 411 and exits from the output major surface 412. Each lens 421, 422 will focus the passing beam 441, 442 at a focal point 443, 444, as would be understood by one skilled in the art.

Referring again to FIG. 1, the effect of the creation of multiple cascaded lenses 104a, 104b, 104c in the active region of the acousto optic device 104 will result in the production of a flying spot at the focus 154a, 154b, 154c of the traveling lens acousto optics device for each of the created lenses. The flying spots 154a, 154b, 154c are then passed through a conventional collimating lens 105, and the group of collimated beams 155a, 155b, 155c are incident onto surface 106a of dichroic mirror 106, but are passed through the dichroic mirror 106. The mirror 106 passes all of the collimated beams 155a, 155b, 155c onto an objective 107 for imaging as a plurality of beams 156a, 156b, 156c onto the surface of the wafer, reticle or other specimen to be scanned 108. The plural parallel beams 156a, 156b, 156c output by the objective 107 are focused onto individual spots 108a 108b 108c on the surface of the wafer, reticle or other specimen and are reflected as parallel beams 157a, 157b, 157c. These reflected beams 157a, 157b, 157c again pass through the objective 107 and are directed onto the back surface 106b of the dichroic mirror 106. These parallel reflected beams 158a, 158b, 158c are reflected by the mirror 106 and are applied to a collimating lens 109.

The beams from the lens 109 are output onto a camera having a multi-stage, multi-tap, vertical transfer CCD 110. The CCD has respective detection areas, 111, 112, 113 that are illuminated by one of the beams 159a, 159b, and 159c. As the beams scan the surface of the wafer 108, and produce parallel image streams, the cells of each sector 111, 112, 113 of the charged couple device 110 capture the output pixels in each respective beam. Each sector 111, 112, 113 of the multi-tap CCD 110 has a respective shift register section 114, 115, 116, which corresponds to the beams 159a, 159b, 159c. These parallel-input sectors may be readout in parallel, thereby increasing the throughput of the image detection device. Thus, in a given period of time, a parallel readout would be implemented by inputting a series of readout pulses to each of the shift registers, thereby causing them to output their content in parallel data streams.

In a general example, the first sector 111 having shift register 114 is readout by a sector transfer signal 160a, which is input through an amplifier 121. The signal is a series of pulses that cause the shift register, whose stages have been loaded in parallel, to readout its data in series through buffer 131 onto output line 161a. Similarly, clocking signals for sector 2 and sector 3 are applied, respectively via amplifiers 122, 123 to the shift registers 115, 116 of the multi-tapped CCD sectors 112, 113. The resulting data that is serially readout via amplifier 132, 133 are provided to data outputs 161b, 161c.

The capture of the back reflected light beams 157a, 157b, 157c from the surface of the wafer or specimen 108 surface by the multi-section tapped linear CCD structure 110 presents a highly effective and efficient design. The structure 110 is built such that the same objective structure is used for the scanning and reflected light. Moreover, when the reflected light from each scanning beam is applied to the segmented CCD structure 110, the content of the information derived from scanning a respective section of the specimen is parallel transferred to a temporary shift register and then readout serially. The transfer from multiple sectors of the CCD 110 can provide a high volume data throughput, which is extremely desirable in wafer inspection systems.

Figure 5:
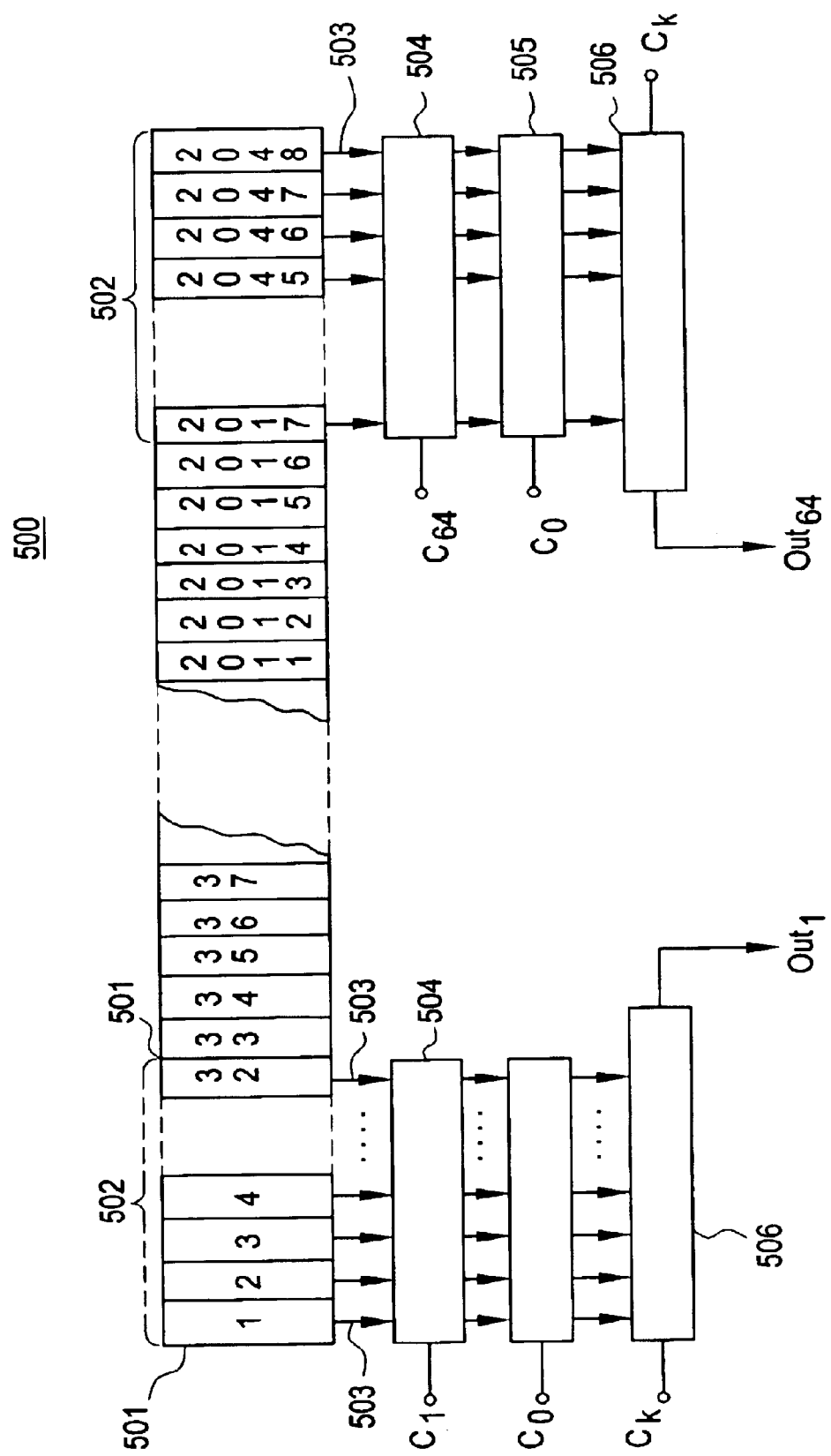
FIG. 5 is a schematic illustration of a multi-stage linear photodiode with a two stage vertical transfer, that would be employed in a CCD scanner according to an embodiment of the present invention.

An exemplary embodiment of a sensor 500 for a practical camera design is illustrated in FIG. 5. The device is a linear CCD having 2048 elements 501, each having a pixel size with a horizontal dimension of 16 $\mu$m and a vertical dimension of 64 $\mu$m, and a pixel pitch of 16 $\mu$. The 2048 elements are divided into 64 independent sections 502 having 32 elements 501 each, with each element 501 having an output 503 that is provided in parallel with the output of the other 31 elements in its section 502 to a first temporary storage stage 504. The sections 502 are disposed immediately adjacent to another section. In an alternative embodiment, there may be 128 outputs with only 16 pixels per tap, to provide higher rates. The 32 values of each first temporary storage stage 504 is read out by a respective clock $C_1$–$C_{64}$ in parallel to a respective second tier storage stage 505 and the 32 values of all second tier storage stages 505 are read out in response to a single clock $C_0$ to a respective readout shift register stage 506. The 32 bytes in each readout shift register stage 506 are clocked out in series by clock inputs $C_K$, and the voltage mode analog output from the register is provided to a respective output port $OUT_1$–$OUT_{64}$ for each of the 64 sections 502. Appropriate voltages are applied to the device for proper operation, as would be understood by one skilled in the art. The sensor with this architecture may be designed to have a data rate of 20–40 MHz (1.0–1.6 MHz line rate) and output in the range of 2.0–3.2 Gpix per second.

Figure 2:
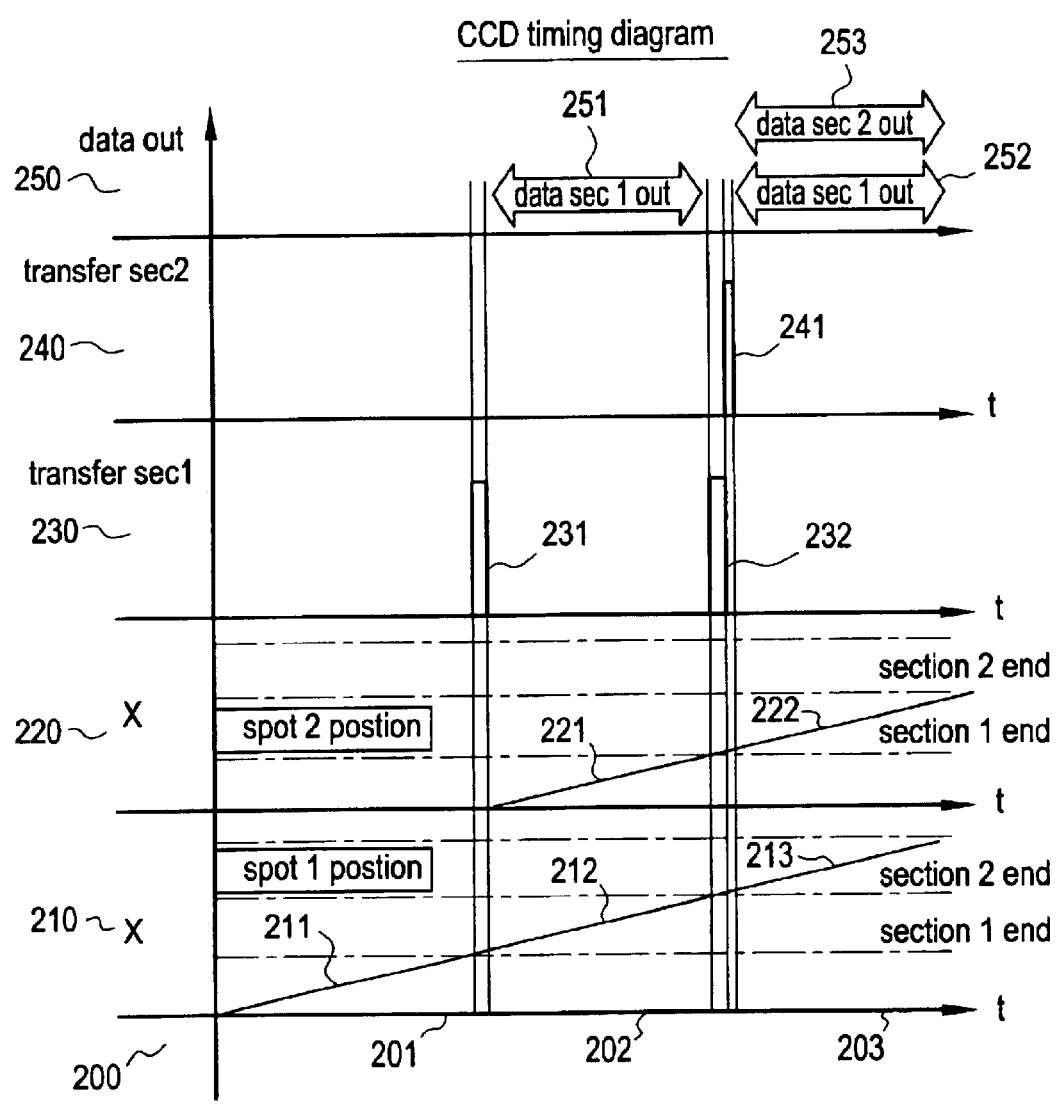
FIG. 2 illustrates an exemplary timing diagram for use of the multiple beams generated by the apparatus of the present invention to scan a wafer or other specimen.

Returning again to the schematic illustration in FIG. 1, the spot timing is so designed that there will be only one spot for a single CCD section 114–116. In fact, in an exemplary embodiment using the linear sensor of FIG. 5 and a 10 beam scanner, only $\frac{1}{6}^{th}$ of the 64 sensor segments, each having storage for 32 pixels, will receive an input at one time. The input of a single beam to plural segments provides a delay that permits the necessary storage and readout processing as the beams move to a subsequent section. By way of example and not limitation, the timing diagram for only two spots is shown in FIG. 2, but may easily be extrapolated to additional spots according to the following teachings. In the Figure, the time (t) line 200 provides a reference for the scan of the surface of a wafer, reticule or other surface by multiple spots. The spot scans along the x (page horizontal) direction while the surface moves at a predetermined velocity in the y (page vertical) direction. Initially, the spot 1 is positioned over a section 1 of the wafer and provides a scan across section 1 of the wafer or other surface, as shown in portion 211 during time period 201. The scan is angled up to the right because of the upward movement of the surface due to movement of the wafer or the like on a stage. The second spot, as illustrated in processing portion 220, has not yet begun to scan. Because only the first spot has scanned during time period 201, there is no data to be transferred from section 1 at processing portion 230 or section 2 at processing portion 240, nor is there data to be output at processing portion 250.

During the second time period 202, the scan of section 1 has been completed by spot 1 and it begins to scan section 2, as indicated by the portion of the scan line 212. Concurrently, the second spot begins its scan of section 1, as indicated by scan line 221. At the beginning of time period 202, all of the data acquired during the scan of section 1 in period 201 is output in parallel at 231. However, because there is no data accumulated for section 2 at this time, there is no input in processing portion 240. However, the data transferred in parallel from section 1 at 231 is serially output during time period 202, as indicated by data section 1 output 251.

At the beginning of period 203, spot beam 1 begins the scan of section 3 at 213 while spot beam 2 begins the scan of section 2 at 222. In processing portion 230, the data accumulated by spot 2 in section 1 is transferred at 232 while the data at spot 1 of section 2 is transferred at 241. During time period 203, the data for each of sections 1 and 2 (gathered by scans 221, 212) are read out serially at 252 and 253, respectively. Clearly, for an exemplary embodiment using 10 beams and having 64 sections of linear scanner, a beam must scan a portion of the surface of the wafer or the like so that at least 6 sections of the CCD receive an input from each beam before returning to begin another scan. Thus, there would be a delay in outputting data comparable to the scan of 6 sections. Synchronization between beam scanning and CCD output would be readily accomplished in order to achieve optimum output.

Figure 3:
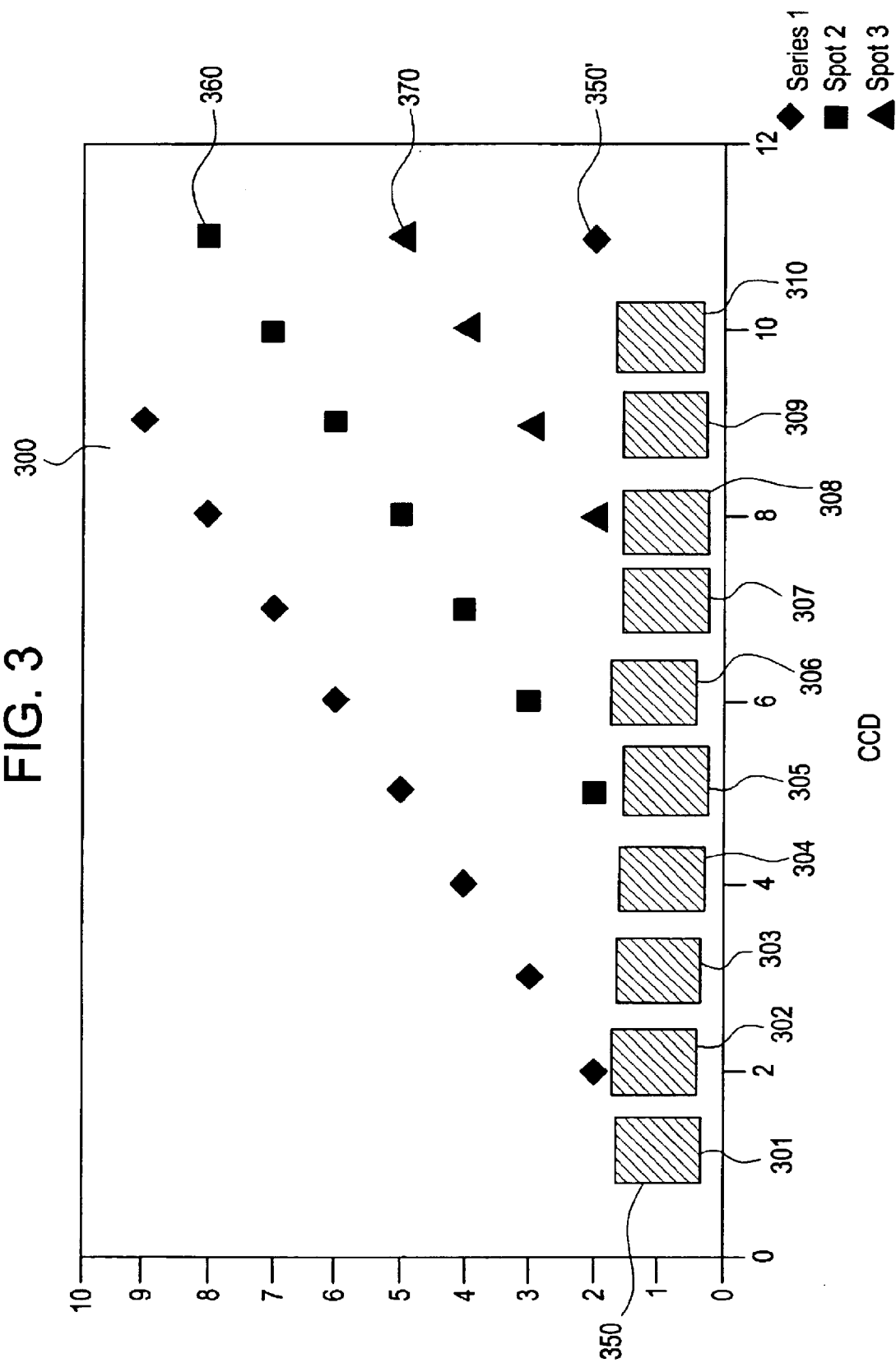
FIG. 3 illustrates the topography of the surface of a wafer as it is concurrently scanned by four beams that are generated in accordance with an exemplary embodiment of the present invention.

FIG. 3 shows the actual surface 300 of a wafer, reticule or similar object under inspection. The divisions 0–12 in the horizontal direction identify the location of individual pixels (light squares 301–312) and several of these pixels (301, 304, 307 and 310) are scan start positions for a scan that proceeds in a direction orthogonal to movement of the wafer, reticule or other object. That movement is in the direction marked by numbers 0–10. The wafer itself will be scanned by a plurality of beams 350, 360 and 370 in a single series, and the beam scan is repeated in subsequent series, as indicated by the beginning of scan series 350' at pixel 10 at the right side of the Figure. As the wafer is moved by a conventional transfer stage apparatus 170 (FIG. 1), which is indicated by the progression of numbers 0–10 vertically, the beams will appear to scan diagonally across the surface of the wafer. Thus, in the first series scan, spot 350 begins at point 301 of sector 1. Then, as it scans, spot 350 moves to pixel 302 of sector 2, pixel 303 of sector 3, etc. The second spot 360 begins at point 304 of sector 1 and moves to point 305 of sector 2, point 306 of sector 3, point 307 of sector 4, etc. Similar movement of spot 370, which begins at point 7 in sector 1. The second series of scans begins with spot 350' again starting, but now at point 310 of sector 1. Similar repetition of the scans of spots 360 and 370 in the second scan will occur, and similar repetition of the scans of spots 350–370 will occur in subsequent series, as the wafer is moved by the stage 170. Given this scanning, a parallel readout of the entire area of the wafer can be seen.

Figure 6A:
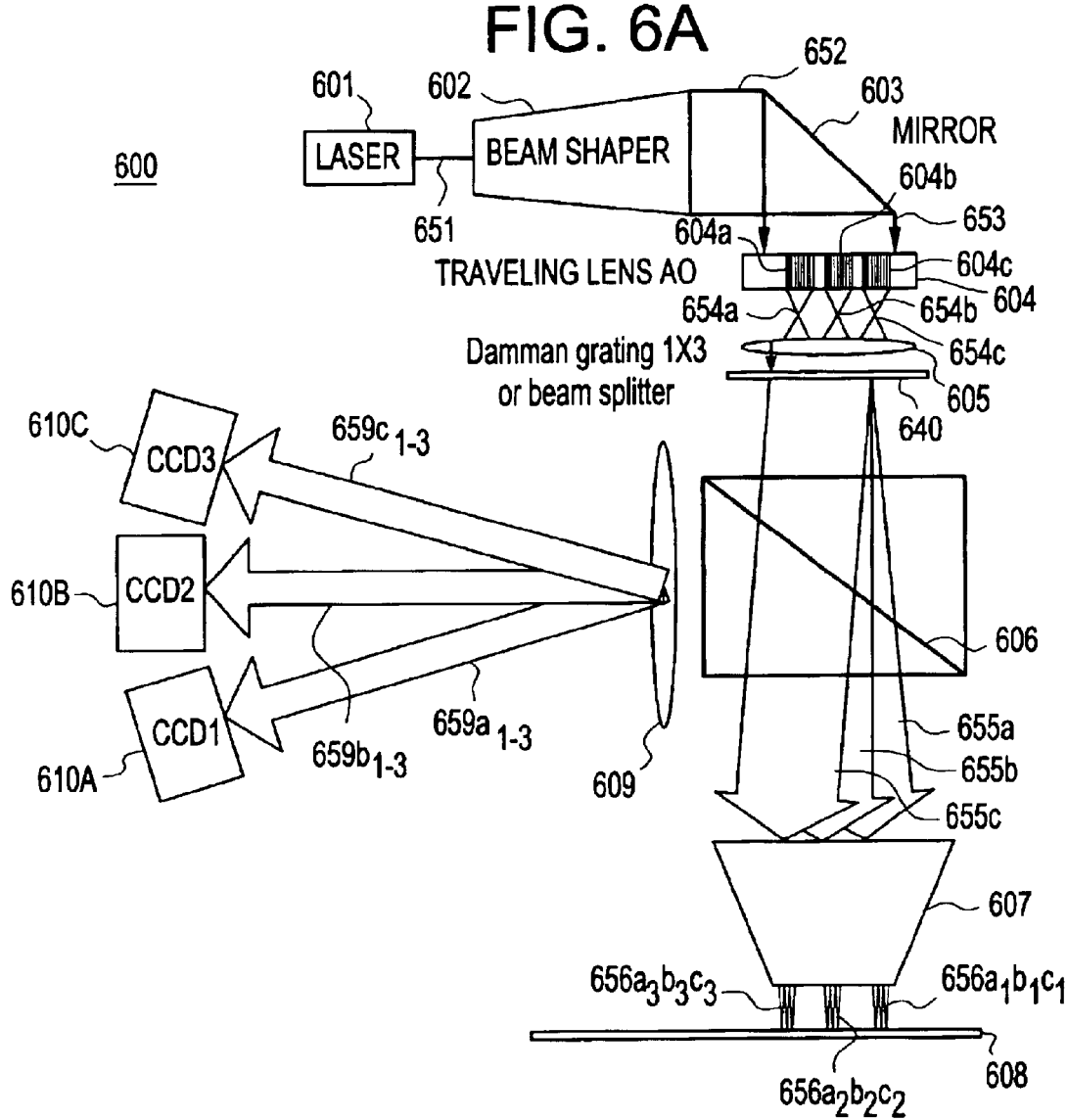
FIGS. 6A and 6B illustrate a schematic representation of a second exemplary system and apparatus for scanning multiple split beams on a wafer or other specimen, and a scanned line structure for the split beams, respectively, in accordance with the present invention.

A second exemplary embodiment is illustrated in FIG. 6A, where the system 600 is substantially the same as the embodiment of FIG. 1, but differs in its use of a beam splitter to create multiple beams from each of the traveling lenses. Specifically, laser 601 produces a light beam output 651 that is applied to a conventional beam shaper 602 to form a beam 652 having a uniform intensity beam profile in a manner known in the art. The collimated beam 652 is applied to a conventional mirror 603, for directing a beam 653 to an operational lens system having an acousto-optic traveling lens 604. The traveling lens acousto-optic device 604 is operative to convert the shaped beam 653 into a plurality of beams 654a, 654b, 654c. Again, while three beams are shown for convenience by way of example, the number of beams may be greater and in an exemplary embodiment may be ten or more concurrently scanning beams. The traveling lens acousto-optic device 604 is responsive to each of a series of chirped RF pulses to form one of multiple cascaded lenses in the active region of the traveling lens device 604. As the RF pulses travel through the device 604, the associated lenses will travel, causing each of their beams to move in the nature of a scan. The multiple cascaded lenses 604a, 604b, 604c in the active region of the acousto optic device 604 will result in the production of a flying spot at the focus 654a, 654b, 654c of the traveling lens acousto optics device, and the flying spots 654a, 654b, 654c are then passed through a conventional collimating lens 605.

Figure 6B:
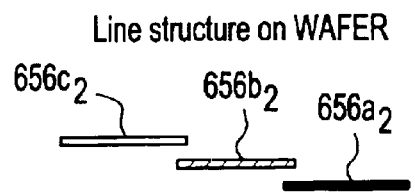

In a departure from the first embodiment, the multiple beams output of the collimated lens 605 are passed through a Damman Grating or beam splitter 640 (a 1×3 type in the illustrated embodiment, but other splitting ratios are also within the scope of this invention), resulting in the generation of several fanned-out beams 655a, 655b, 655c. The split may be performed by any means known in the art, so long as the energy of each split beam is substantially equal. Each of these beams comprises a plurality of spot beams ($655a_{1-3}$, $655b_{1-3}$, $655c_{1-3}$—not shown) that are incident onto surface of dichroic mirror 606, and are passed onto an objective 607 for imaging as a plurality of beams $656a_{1-3}$, $656b_{1-3}$, $656c_{1-3}$ onto the surface of the specimen to be scanned 608. The plural parallel beams $656a_{1-3}$, $656b_{1-3}$, $656c_{1-3}$ output by the objective 607 are focused onto areas 608a, 608b, 608c on the surface of the specimen. Each of the areas is scanned by a separate flying spot originating from a separate one of beams 655a, 655b and 655c, and in an exemplary embodiment, produce an scan line structure as illustrated in FIG. 6B, where the scans from separate beams $656a_2$, $656b_2$, $656c_2$ are clustered but are offset in time and position. These scans are returned as parallel beams (three beams with three scans each—not shown) that again pass through the objective 607 and are directed onto the back surface of the dichroic mirror 606. These parallel reflected beams are reflected by the mirror 606 and are applied to a collimating lens 609.

The beams $659a_{1-3}$, $659b_{1-3}$, $659c_{1-3}$ from the lens 609 are output onto three cameras, each having a respective multi-stage, multi-tap, vertical transfer CCD 610A. 610B, 610C, having a structure and function like that of the linear CCD in the embodiment of FIG. 1. This architecture further increases the throughput and resolution of the image detection device.

Figure 7A:
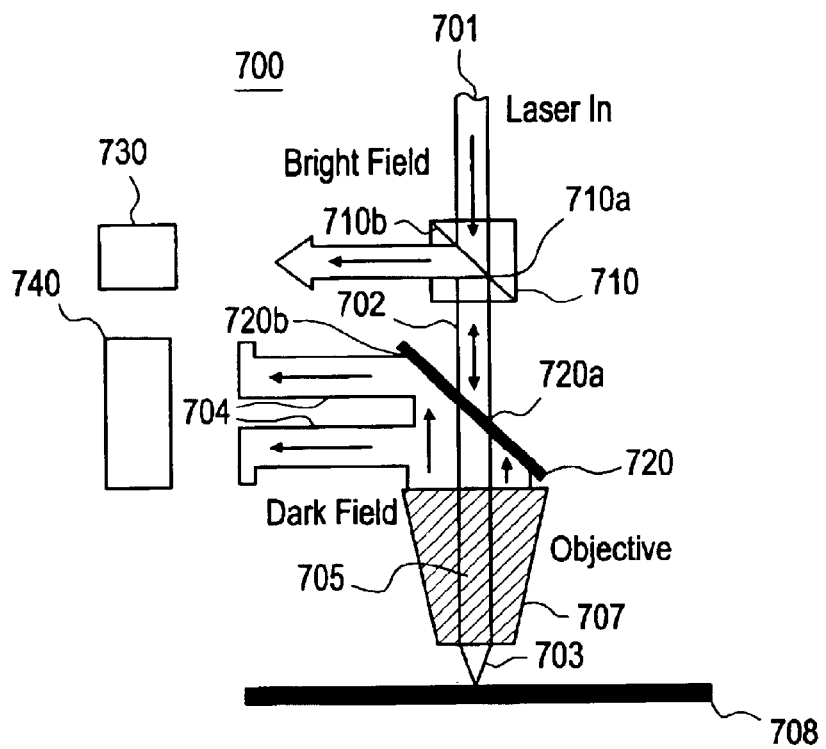
FIGS. 7A and 7B provide a schematic illustration of a single illumination laser and an annular illumination laser architecture for the separate detection of bright field and dark field images on a specimen surface.
Figure 7B:
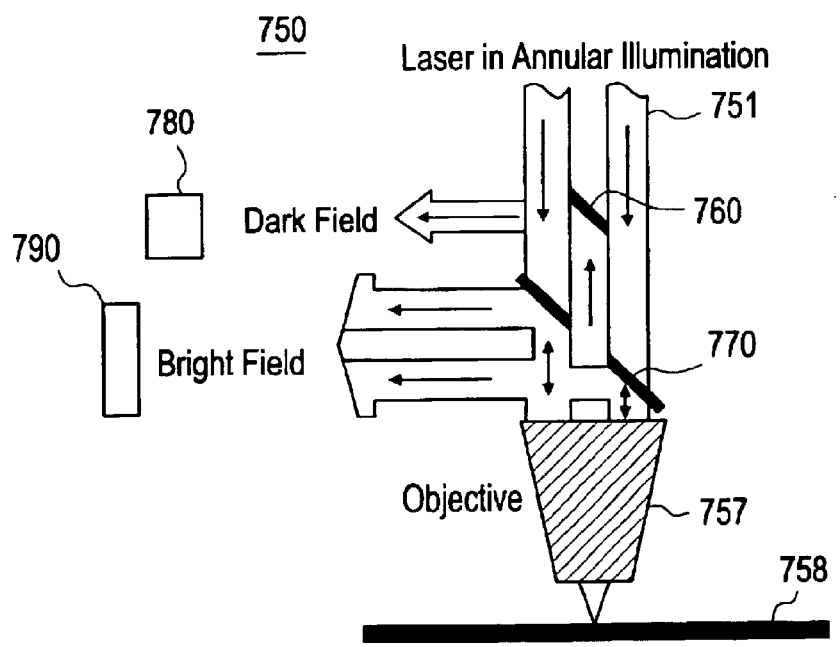

In yet another exemplary embodiment as illustrated in FIG. 7A, laser light from a source, which may include multiple flying spots as already disclosed or a single spot, may pass through a first dichroic mirror 710. The mirror 706 will pass the laser light 701 through a first surface 710a but reflect bright light from an opposite surface 710b. The passed laser light 702 will pass through a second dichroic mirror, having a first surface 720a that passes laser light and a second surface 720b that reflects dark field light 704. The laser light 703 that impacts on the surface of a specimen 708 will be reflected back as dark field light 704 and bright field light 705. The dark field light 704 is separated from the bright field light 705 by surface 720b of dichroic mirror 720, which reflects dark field light and passes bright field light. The dark field light 704 is detected by a photomultiplier tube (PMT) 740, which has high sensitivity. Such PMT, which is of a conventional design and is available from vendors Hammamatsu and Burle, is particularly advantageous where there is dark field low light scattering. The bright field light passes through the mirror 720 and is reflected by surface 710b toward a CCD 730, which may be a multi-stage or single stage CCD, having lower sensitivity but larger dynamic range and higher speed than the PMT.

In an alternative embodiment, a laser 751 in an annular illumination form, which may be scanned by a traveling lens in accordance with principles already disclosed herein, is provided past a dichroic mirror 760 and dichroic mirror 770 to objective 757 for focusing onto the surface of a specimen 758. The reflected light representing dark field and bright field components, is directed onto the surface of mirror 770, and bright field light is reflected toward a CCD 790. The dark field light is passed through the mirror 770 toward mirror 760, whose surface reflects the light to a PMT 780 for detection.

While the present invention has been described with respect to certain exemplary embodiments, it is not limited thereto, and the full scope of the present invention is defined in the appended claims, as interpreted in accordance with applicable law.

We claim:

1. A system for inspecting a specimen comprising:
   a light source providing a beam;
   a traveling lens acousto-optic device having an active region and responsive to an RF input signal to concurrently generate plural traveling lenses in said active region, each lens having a focus, said traveling lens acousto-optic device being operative to receive the light beam and generate plural flying spot beams, at the respective focus of each of the generated traveling lenses;
   at least one light detector comprising a plurality of detector sections, each detector section having a plurality of light detectors and at least one multi-stage storage device operative to receive in parallel an input from said plurality of light detectors and to serially read out information stored in said multiple stages.

2. The system as claimed in claim 1, further comprising a source of said RF input signals, said signals comprising chirped RF pulses, each pulse operative to generate a propagating lens in said active region.

3. The system as claimed in claim 1 further comprising a beam splitter operative to receive a first plurality of plural flying spot scanning beams and divide each said beams into a second plurality of flying spot scanning beams.

4. The system as claimed in claim 1 wherein said light source is a UV laser and further comprising a beam shaper disposed in a light path between said UV laser and said traveling lens acousto-optic device.

5. The system as claimed in claim 2 wherein said at least one light detector comprises a plurality of multi-section CCD devices.

6. The system as claimed in claim 1 wherein said at least one light detector comprises a CCD for bright field detection and a PMT for dark field detection.

7. The system as claimed in claim 1 wherein each said detector sections comprises a temporary shift register having plural stages, said shift register being operative to receive in each stage in parallel the content of a corresponding detector and to be read out serially.

8. The system as claimed in claim 7, further comprising a source of section transfer signals, said source providing section transfer signals to read our said stages in series, and a data out line, including a buffer, to carry said serial read out signals.

9. A system for inspecting a specimen comprising:
a source of a plurality of concurrently and independently controlled scanning spot beams, said beams being imaged on a surface of said specimen and a plurality of reflected beams being produced therefrom;
at least one light detector, said at least one detector comprising a plurality of detector sections, each detector section having a plurality of light detectors and at least one multi-stage storage device operative to receive in parallel an input from said plurality of light detectors and to serially read out information stored in said multiple stages.

10. A system for inspecting a specimen comprising:
a source of a plurality of concurrently and independently controlled scanning spot beams, said beams being imaged on a surface of said specimen and a plurality of reflected beams being produced therefrom;
at least one light detector, said at least one detector comprising a plurality of detector sections, each detector section having a plurality of light detectors and at least one multi-stage storage device operative to receive in parallel an input from said plurality of light detectors and to serially read out information stored in said multiple stages, wherein each said light detector section comprises an input for a section transfer signal and an output for serial readout of said section.

11. A system for inspecting a specimen comprising:
a source of a plurality of concurrently scanning spot beams, said beams being imaged on a surface of said specimen and a plurality of reflected beams being produced therefrom;
at least one light detector, said at least one detector comprising a plurality of detector sections, each detector section having a plurality of light detectors and at least one multi-stage storage device operative to receive in parallel an input from said plurality of light detectors and to serially read out information stored in said multiple stage, wherein said source of a plurality of scanning spot beams comprises an acousto-optic traveling lens device having a single crystal for providing a plurality of traveling lenses to generate said plurality of beams.

12. The system as claimed in claim 11, wherein said acousto-optic traveling lens device generates said lenses in response to a series of chirped RF signals.

13. The system as claimed in claim 12, further comprising a traveling stage for said specimen, wherein said series of chirped RF signals are timed to produce a scan coordinated with movement of said traveling stage.

14. A method for inspecting a specimen comprising:
providing a plurality of flying spot beams from a single source of light;
scanning, by independently controlling, said plurality of flying spot beams on a surface of a specimen, whereby a corresponding plurality of reflected beams are generated;
capturing and storing the content of each of said reflected beams simultaneously in a respective signal storage section; and
serially reading out the stored signals from a plurality of said storage sections concurrently.

15. The method as claimed in claim 14
wherein said scanning step comprises concurrently scanning respective ones of said plurality of beams over different sections of said specimen.

16. A method for inspecting a specimen comprising:
providing a plurality of flying spot beams from a single source of light;
scanning said plurality of flying spot beams on a surface of a specimen, whereby a corresponding plurality of reflected beams are generated;
capturing and storing the content of each of said reflected beams simultaneously in a respective signal storage section; and
serially reading out the stored signals from a plurality of said storage sections concurrently,
wherein said scanning step comprises inputting a series of chirped RF signals, each chirped RF signal controlling the scanning of a respective one of said plurality of spot beams.

17. A method for inspecting a specimen comprising:
providing a plurality of flying spot beams from a single source of light;
scanning said plurality of flying spot beams on a surface of a specimen, whereby a corresponding plurality of reflected beams are generated;
capturing and storing the content of each of said reflected beams simultaneously in a respective signal storage section; and
serially reading out the stored signals from a plurality of said storage sections concurrently,
wherein said scanning step comprises concurrently scanning respective ones of said plurality of beams over different sections of said specimen,
further comprising:
during a first period, scanning a first spot beam across a first section of a specimen surface and storing information from said first beam scanning of said first section; and
during a second period,
(a) scanning said first spot beam across a second section of a specimen surface, said second section being adjacent to said first section, and storing information from said first beam scanning of said second section;
(b) reading out serially the information from said first beam scanning stored during said first period; and
(c) scanning a second spot beam across said first section of said specimen surface and storing information from said second beam scanning of said second section.

18. The method as claimed in claim 17, further comprising during a third period:
(d) scanning said first spot beam across a third section of a specimen surface, said third section being adjacent to said second section, and storing information from said first beam scanning of said third section;
(e) reading our serially the information from said first beam scanning stored during said second period and reading out serially the information from said second beam scanning stored during said second period; and
(f) scanning said second spot beam across said second section of said specimen surface and storing information from said second beam scanning of said second section.

19. The method as claimed in claim 14, further comprising passing a first plurality of flying spot scanning beams through a beam splitter and creating a second plurality of flying spot scanning beams.

20. A method for inspecting a specimen comprising:

providing a plurality of flying spot beams from a single source of light;

scanning said plurality of flying spot beams on a surface of a specimen, whereby a corresponding plurality of reflected beams are generated;

capturing and storing the content of each of said reflected beams simultaneously in a respective signal storage section; and serially reading out the stored signals from a plurality of said storage sections concurrently, further comprising varying an RF signal to provide selective traveling lenses.

21. The method as claimed in claim 14 wherein said scanning further comprises moving said specimen.

22. A method for inspecting a specimen comprising:

providing a plurality of flying spot beams from a single source of light;

scanning said plurality of flying spot beams on a surface of a specimen, whereby a corresponding plurality of reflected beams are generated;

capturing and storing the content of each of said reflected beams simultaneously in a respective signal storage section; and serially reading out the stored signals from a plurality of said storage sections concurrently, wherein said reflected beams comprise bright field and dark field components, said method further comprises separating said bright field and dark field components, and said step of capturing and storing comprises capturing said bright field components with a CCD and capturing said dark field components with a PMT.

23. The method as claimed in claim 22 wherein said step of separating is performed with at least one dichroic mirror.

24. The method as claimed in claim 22 wherein said step of separating is performed with at least one dichroic mirror.

25. The system as claimed in claim 6 wherein at least one CCD is for bright field detection and at least one PMT is for dark field detection.

* * * * *